(12) United States Patent
Knapp

(10) Patent No.: US 6,278,999 B1
(45) Date of Patent: Aug. 21, 2001

(54) INFORMATION MANAGEMENT SYSTEM FOR PERSONAL HEALTH DIGITIZERS

(76) Inventor: Terry R. Knapp, 7451 N. 63$^{rd}$ St., Longmont, CO (US) 80503

(*) Notice: Subject to any disclaimer, the term of this patent is extended or adjusted under 35 U.S.C. 154(b) by 0 days.

(21) Appl. No.: 09/096,717

(22) Filed: Jun. 12, 1998

(51) Int. Cl.$^7$ .................................................. G06F 17/30
(52) U.S. Cl. ...................... 707/9; 707/3; 707/4; 707/6; 709/201; 709/203; 705/2; 705/3
(58) Field of Search .................................... 707/9, 3, 4, 6; 709/203, 201; 705/2, 3

(56) References Cited

U.S. PATENT DOCUMENTS

| 5,544,661 | * | 8/1996 | Davies et al. | 128/700 |
| 5,619,991 | | 4/1997 | Sloane | 600/300 |
| 6,014,666 | * | 1/2000 | Helland et al. | 707/9 |
| 6,018,713 | * | 1/2000 | Coli et al. | 705/2 |

FOREIGN PATENT DOCUMENTS

WO98/02837  1/1998  (WO).

* cited by examiner

Primary Examiner—Jack Choules
Assistant Examiner—Cheryl Lewis
(74) Attorney, Agent, or Firm—Duft, Graziano & Forest, P.C.

(57) ABSTRACT

The present information management system for personal health digitizers. This system provides a centralized database that collects and stores monitoring data from a large number of individuals who are termed "consumers" herein. The information management system for personal health digitizers includes processing elements that can be used to perform statistical analysis of the collected data on a per consumer, population segment, or query specific basis. The analysis function is made available to various classes of "users" which classes can include consumers, medical practitioners, health care providers, institutions, and the like. The database is architected in a hierarchical manner to enable the users to access only the relevant, prepartitioned segment of the collected data that this particular class of user is authorized to analyze. Thus, the privacy of the consumer data is maintained by prohibiting access to this individuals data except to users who are specifically authorized by the consumer. In addition, the granularity of the data made available to the various classes of users is selected to prevent the users from deriving information about the consumer population that they are not entitled to receive.

18 Claims, 10 Drawing Sheets

FIG. 1

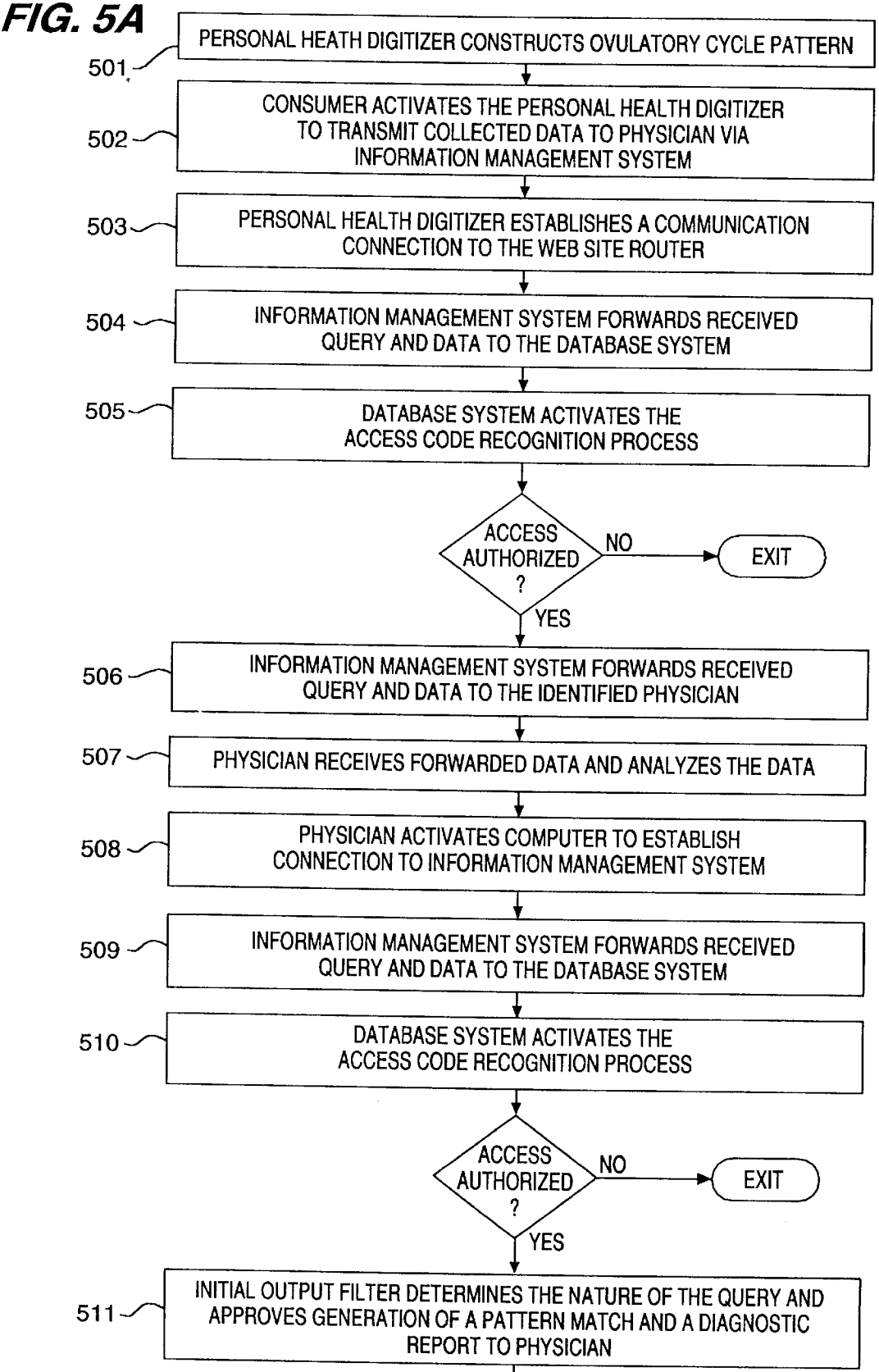

INFORMATION MANAGEMENT SYSTEM FOR PERSONAL HEALTH DIGITIZERS

FIELD OF THE INVENTION

This invention relates to medical monitoring systems and, in particular, to a centralized hierarchical information management system that functions to collect data over a communication medium from numerous patients and their personal health digitizers for processing and analysis.

Problem

In the field of medical monitoring systems, the traditional measurement paradigm is that of a professional medical practitioner performing measurements, including diagnostic tests, of a patient's physiological characteristics in a controlled environment. These measurements are typically taken on an infrequent basis and generally in response to the patient perceiving that they had encountered a medical problem of a sufficiently severe nature to justify the time and cost of consulting a medical practitioner. It was in the best interest of the professional medical practitioner to perform these measurements in the most accurate manner since the opportunity for data collection may be limited to the single patient visit. Therefore, the measurements or tests were either performed in the office of the medical practitioner or a hospital/laboratory setting using monitoring instruments that are precisely maintained by the professional medical practitioner and/or trained technical support staff. This environment reduces the probability that inaccurate measurements are taken. However, the measurements taken represent only a single point in time view of the patient, without any indication of the baseline measurements that are "normal" for that patient. These isolated measurements provide only limited information to the medical practitioner and often do not indicate temporal variations or subtle anomalies in the physiology of the patient. The medical practitioner can therefore only recognize gross anomalies that are indicative of the presence of a significant problem. This medical monitoring paradigm does not lend itself to the early detection and identification of medical problems, especially those of a transient or intermittent nature, due to the limited data base with which the medical practitioner has to work.

The Advent of Home-Use Biosensors

The new paradigm in the field of medical monitoring systems is for patients to perform their own measurements to reduce the cost and inconvenience of scheduling an appointment with a professional medical practitioner. The patients perform simple non-invasive measurements using sensors that are either single use disposable elements or multi-use elements. Patients have had access to home-use biosensors for many decades. The common thermometer is an example. This "biosensor" measures a person's core temperature, an analog indicator of physiological status. That information is revealed to the patient who then makes a health care related decision. In recent years, biosensors for home use have taken many forms, such as apnea (breathing difficulty) monitors, urine test kits for pregnancy or ovulation detection, glucose monitors for diabetics, etc. Most of these monitors have reflected the analog basis of the measurement (e.g., change in color of a test strip). Conception Technology Incorporated produces a biosensor (OvuSense product) that measures the electrochemical changes driven by reproductive hormones, converting the analog data to digital format.

The fact that home use biosensors are increasingly sophisticated and diverse as well as affordable attests to a large market opportunity that will continue to expand, as personal information about the condition of one's body acquired in the privacy of the home empowers the user relative to appropriate health care decision-making. Sensors that provide digital data, unlike analog test strip devices or mercury thermometers, open up the possibilities inherent in digital data analysis, storage, transmission, etc. The above-noted OvuSense product is representative of this new class of home-use digital-readout biosensors, which are termed Personal Health Digitizers (PHD's) herein.

Telecommunications Technology

Digital communications for nearly all information signals is rapidly supplanting older analog technology. Moreover, the infrastructure for moving very large amounts of data continues to improve. Medical telecommunications, or "telemedicine", is simply the transmission of medical data and information over these established communication channels. Real-time transmission of digital data now enables the transmission not only of text, but also medical photographs and complex medical information such as X-rays, CAT scans, and cardiac catheterization sessions from remote sites to centers of advanced expertise for interpretation and feedback.

The Holter Monitor for continuous recording of a person's electrocardiogram to detect only occasional (but perhaps deadly) dysrhythmias served as a forerunner for the types of home use monitoring that is now increasingly commonplace. The Holter Monitor not only could provide a continuous record of cardiac activity, but could telecommunicate its recorded patterns over telephone lines to the doctor's office.

Recently, the CheckMate line of home glucose monitors from Cascade Medical, Inc., together with its companion CheckLink telemedicine module, exemplify the expanding possibilities of acquiring direct physiological reading from home users and allowing the telecommunication of that information to the user's doctor or clinic of choice. Communication of this sort allows users to adjust diabetes therapy without the inconvenience and expense of office visits and central laboratory tests.

Information and Information Management (Informatics) In Medicine

The chief impediment to widespread adoption of current electronic information capability by mainstream medicine lies at the doctor-patient interface. Impediments include standardization of data gathering protocols, lack of point-of-care, user-friendly data entry mechanisms, etc. These impediments are being addressed by myriad companies, albeit slowly. There are, however, two emerging societal trends in the U.S. that are poised to drive medical informatics in another direction: the consumer's demand to know, coupled with consumer distrust of the managed care environment.

Certainly, the medical practitioner's ability to manage the informed patient is enhanced if the medical practitioner is the source of the information. Increasingly, consumers are looking elsewhere. Unfortunately, no matter how much information about a specific disease or condition a consumer accumulates, the lay person is not equipped to apply Fat information directly in the care of their own or a loved one's problem. Despite information, they lack the knowledge, expertise and sense of proportion, as well as the pertinent, necessary diagnostic data upon which to base a therapeutic decision.

Another aspect of this problem is that all of the presently available telemedicine systems are point-to-point in nature, in that they require the patient to establish a data communication connection over the telephone lines to the medical practitioner's office to transfer information. The inconvenience of such a protocol renders this procedure impractical for routine data collection or data collection relating to non-life threatening medical problems and requires interpretation and report to the consumer by the physician. The sensors used for data collection relating to these types of situations are used only for the edification of the patient or infrequent data communication to the medical practitioner. However, to make such sensors effective in the detection and diagnosis of problems, the data that is collected by the patient must be accurate in nature, frequent and periodic in collection, and communicated to the medical practitioner in a timely manner. Furthermore, the data collected should include sufficient baseline data to enable the medical practitioner to detect anomalies in the pattern of data that is collected over time. However, there is presently no mechanism available to collect data on a frequent basis and communicate this data to the medical practitioner, or to perform an automated pattern analysis function on such data, if collected, or to automate a report to the consumer.

Solution

The above described problems are solved and a technical advance achieved in the field by the present information management system for personal health digitizers. This system provides a centralized database that collects and stores monitoring data from a large number of individuals who are termed "consumers" herein. The information management system for personal health digitizers includes processing elements that perform statistical analysis of the collected data from any of numerous viewpoints, such as on a per consumer, population segment, or query specific basis. Thus, the information management system collects a statistically valid volume of data from numerous consumers and performs pattern matching and other statistical analyses on this data in a multi-dimensional manner to thereby deliver relevant information to the various classes of users who access the information management system.

The analysis function is made available to various classes of "users" which classes can include consumers, medical practitioners, health care providers, institutions, and the like. The database is architected in a hierarchical manner to enable the users to access only the relevant, prepartitioned segment of the collected data screened for appropriate analysis for that particular class of user authorized to receive this analysis. Thus, the privacy of the consumer data is maintained by prohibiting access to this individual's data except to users who are specifically authorized by the consumer. In addition, the granularity of the data made available to the various classes of users is selected to prevent the users from deriving information about the consumer population that they are not entitled to receive.

This information management system assigns a user-access code to each class of user to thereby control the level of access and data interpretation capability. The consumer communicating via the home-use Personal Health Digitizer is automatically assigned an access code that reflects the consumer's lay-user status. The lay-user code, coupled with the Personal Health Digitizer's unique serial number allows information management system queries and responses based on the consumer's individual pattern, providing, for example, interpretation against the broad base of data and its patterns as collected from many consumers. The interpretation filters that are provided in the present information management system for personal health digitizers are specific to each class of user-access code. For lay-users, the restrictions inherent in their access codes results in pattern interpretation that is expressed in general terms, in lay language with appropriate disclaimers and suggestions regarding supplemental medical practitioner interpretation.

The interpretive filter for provider-specific access codes (those providers who subscribe to the database and have Personal Health Digitizer-specific interpretive software) allows detailed and highly specific interpretation of an individual consumer's patterns weighed against the pattern databank. Specific diagnostic interpretations and expert-system generated therapeutic suggestions may be obtained at provider request. Institutions such as managed care organizations, insurance companies, National Institute of Health, World Health Organization and others have subscriber access limited to epidemiological type analyses of patterns based on the limitations interposed by filters applied via access codes assigned to this class of institutions. In this way, the managed care organization may, for example, determine the types of diseases or conditions in a specific geographic, age-range, sex determined or other cohort-based set of criteria predicated on the particular type of Personal Health Digitizer-generated database content. In this manner, anticipated cost-of-care for population subgroups may be determined, actuarial decisions may be made, and other such decisions made based upon current and statistically valid population data. The individual consumer's data is protected, as is the individual from the consequence of a directed decision from an institution—such as an insurance company denying individual coverage based on specific Personal Health Digitizer data.

As an example of the applicability of the information management system and a particular use, the OvuSense Monitor, with its companion OvuLink Base Station, disclosed herein serves to introduce improved functionality to the reproductive medicine field. The OvuSense Monitor acquires data that predicts and detects ovulation directly from the woman's body, allows her to use that data for her own decision-making relative to conception of a child. Furthermore, the consumer can transmit the data from the OvuLink Base Station, or via a personal computer, to the information management system to allow the consumer to share the information with a fertility specialist or clinic if she requires medical help in conceiving. Because timing for visits to the fertility clinic is inexact, a number of these visits typically result in wasted time and money. The telecommunication of detailed information about the woman's reproductive system to the medical practitioner therefore is a more efficient mode of information gathering. The information management system and its capabilities to process the collected data provide information to the consumer that is not usually obtainable other than in a clinic situation and this system can be extremely efficient in both cost and time for both the woman and her doctor.

BRIEF DESCRIPTION OF THE DRAWING

FIGS. 2 and 3, 4 and 5A–5B 6 and 7 illustrate in block diagram and flow diagram form, respectively, the operation of the present information management system for personal health digitizers to process information requests from consumers, physicians and institutions, respectively;

DETAILED DESCRIPTION

Figure 1:
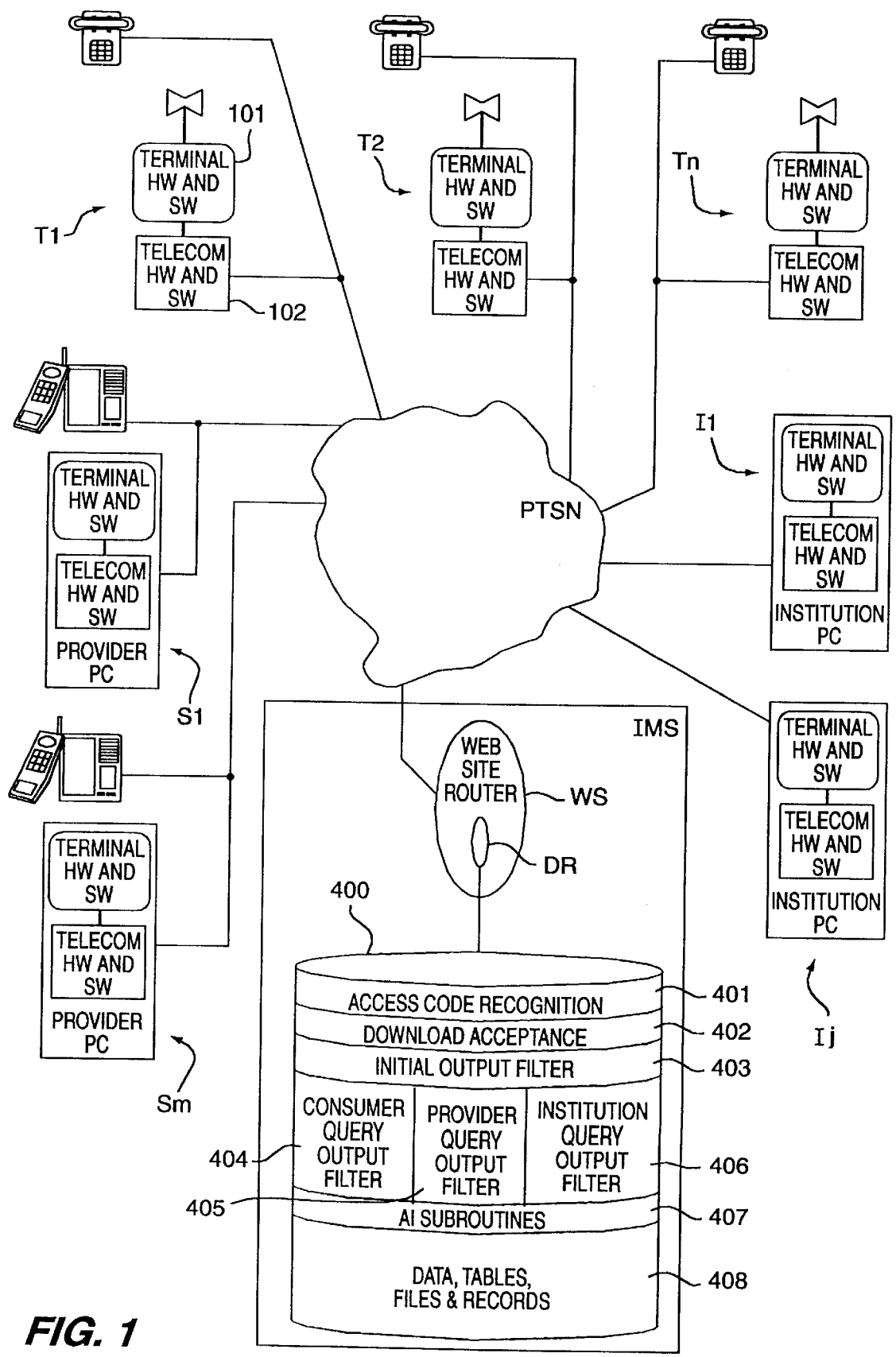
FIG. 1 illustrates in block diagram form the overall architecture of the present information management system for personal health digitizers.

FIG. 1 illustrates in block diagram form the overall architecture of the present information management system for personal health digitizers, termed "information management system" herein that collects data from numerous remotely located data sources T1-Tn. The information management system IMS comprises a data storage and processing complex that is connected to at least one communication medium PTSN to thereby enable customers to obtain data communication connections with the information management system IMS. The customers are typically equipped with a Personal Health Digitizer and may also be equipped with a processing element, such as a personal computer, collectively termed "terminal equipment" T1-Tn herein. The consumer performs non-invasive monitoring procedures on themselves or other household members using the Personal Health Digitizer T1-Tn. The personal Health Digitizer T1-Tn provides a readout and/or interpretation using its own internal processor. The data collected in this procedure may then be downloaded to the information management system IMS via the personal computer or directly using the Personal Health Digitizer T1-Tn. The data communication connection can be via the Internet, using the well known personal computer modem and Internet browser technology available at the personal computer to communicate with the interactive web site WS and its communications and data router DR. Alternatively, the data communication connection between the consumer terminal equipment T1-Tn and the information management system IMS can be via the Public Telephone Switched Network (PTSN). For the purpose of this description, the Internet data communication connection is used as the example to illustrate the operation of the information management system IMS.

In addition to the individual customers at terminal equipment T1-Tn, there are numerous other users that can access the information management system IMS. These users include health care providers at their terminal equipment or servers S1-Sm, institutions via their terminal equipment and servers I1-Ij, and the like. The various users each can use the communication network PTSN to access the information management system IMS and its analysis function based upon the predefined class of "users" which classes can include consumers, medical practitioners, health care providers, institutions, and the like. The database 400 is architected in a hierarchical manner to enable the users to access only the relevant, prepartitioned segment of the collected data that the particular class of user is authorized to receive. Thus, the privacy of the consumer data is maintained by prohibiting access to this individual's data except to users who are specifically authorized by the consumer. In addition, the granularity of the data made available to the various classes of users is selected to prevent the users from deriving information about the consumer population that they are not entitled to receive. This access control is enforced by the use of a plurality of filters 403–406, each of which is architected to provide customized access to a selected one of the classes of users that can access the information management system IMS, as described below.

Information Management System Architecture

The information management system IMS comprises a database 400 that stores and manages the data collected from the consumers. The data is typically stored in database 400 on a mass storage system to enable the associated database processors to have efficient shared access to this data. The database processors include data processing algorithms 408 that operate on the raw physiological data that is collected from the individual consumers to produce additional data that is indicative of cyclic patterns for the individual consumers or anomalies in their collected data that are indicative of potential physiological problems. In addition, interpretive processing systems 407 are provided to analyze the collected data for patterns. These interpretive processing systems 407 can be standard software database processes or neuromorphic systems such as expert systems, neural networks, and the like. These systems perform pattern recognition operations on the collected data to identify correlations among the data using cohort-based sets of criteria.

Personal Health Digitizer—OvuSense System

Figure 8:
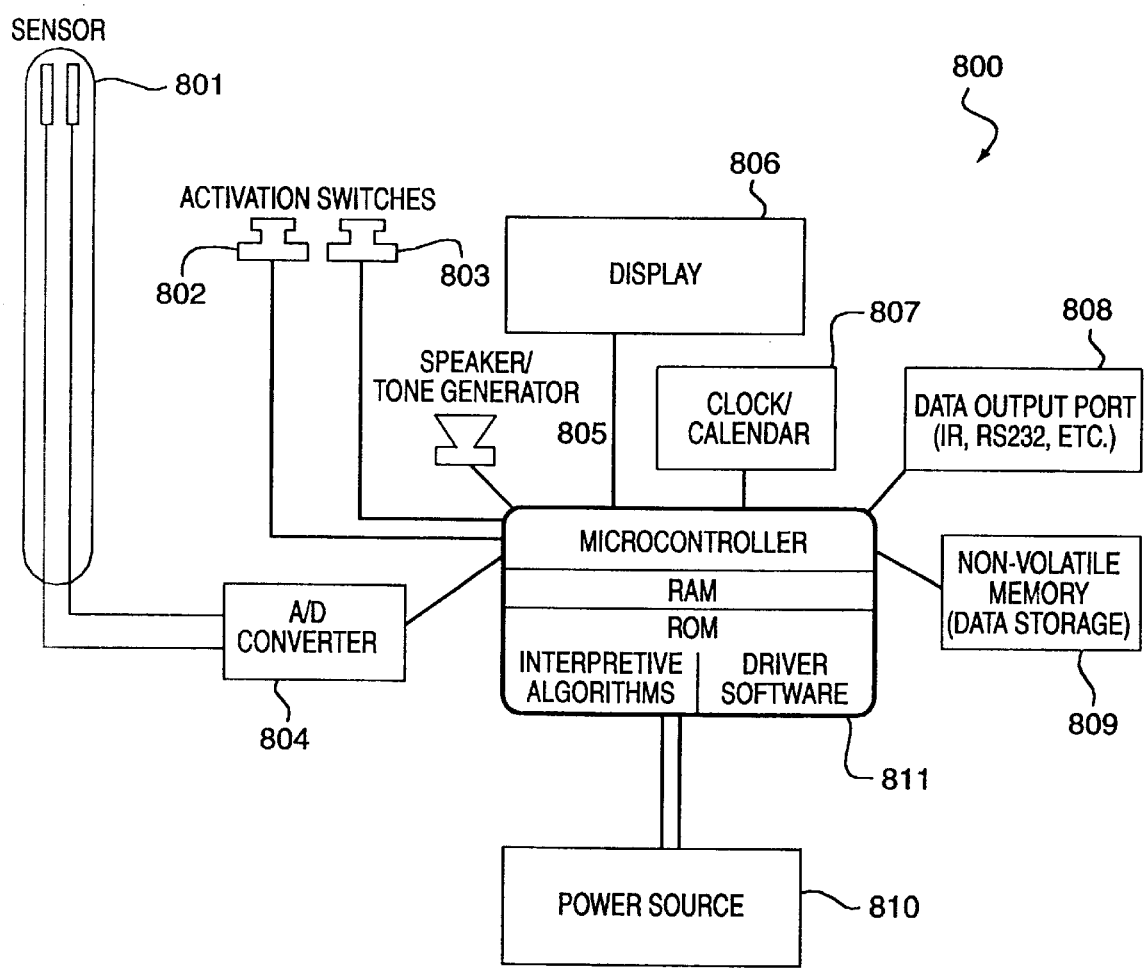
FIG. 8 illustrates an example of a specific personal health digitizer that is used with the present information management system for personal health digitizers.

As shown in FIG. 8, each of these personal health digitizers is designed for mass-market home use, with the example used being the OvuSense personal health digitizer that produces detailed pattern generation to assist a woman in determining her precise fertility window, and variances therefrom, for conception purposes. Alternatively, the personal health digitizer can incorporate internal artificial intelligence software to "learn" an individual user's cyclic pattern so that a simple icon-driven, "red light—green light" indication of fertility status can serve as a contraception aid. Both instruments are capable of storing all cyclic data obtained by the user for the entire three-year useful life of the product. The OvuSense, because a fertility patient frequently is under the care of a fertility specialist, incorporates telemedicine and data download capabilities to a personal computer (either the user's home personal computer or, via telecommunication, the fertility specialist's personal computer) or a stand-alone pattern-graphing, modem-containing OvuLink Base Station.

Figure 9:
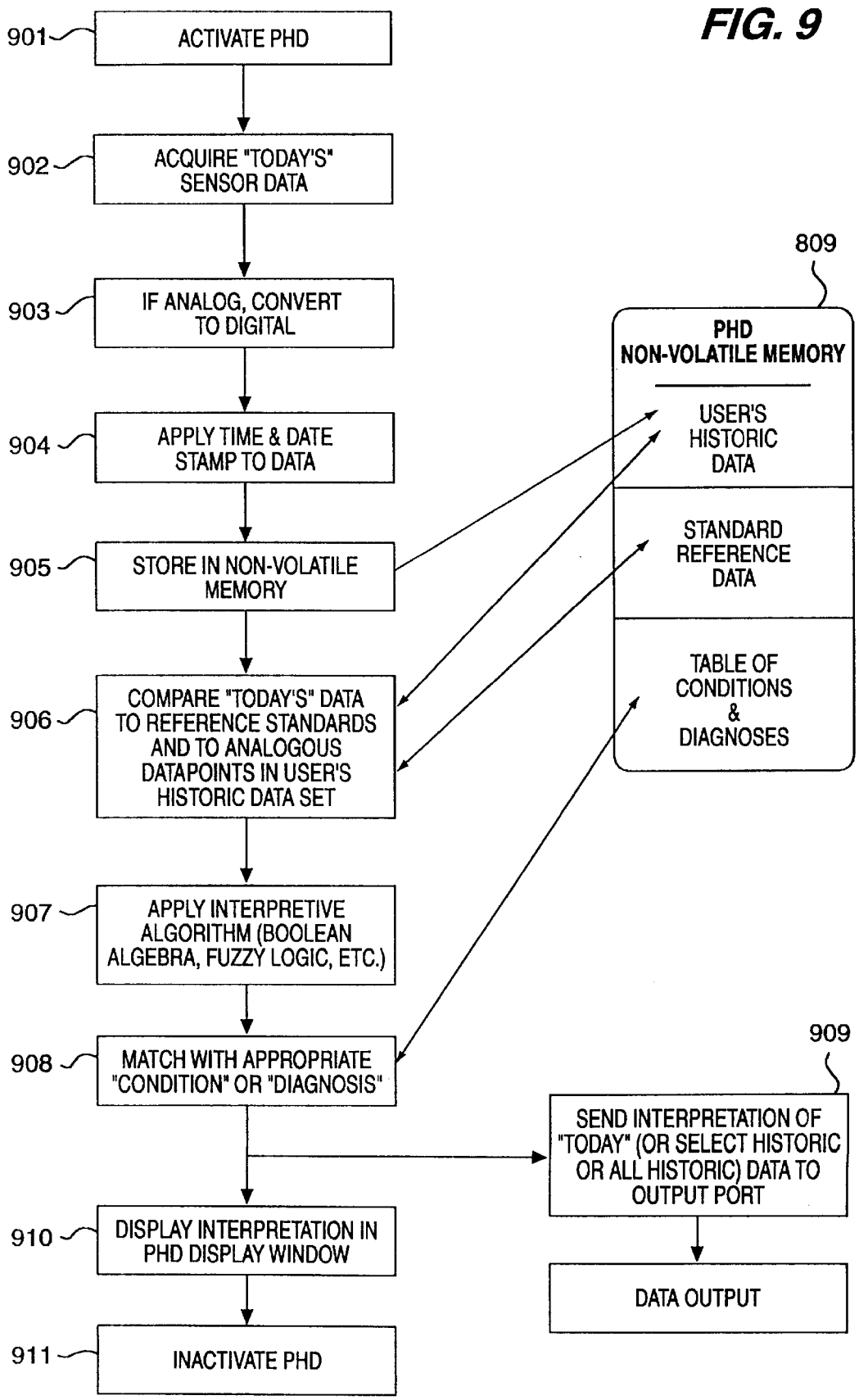
FIG. 9 illustrates in flow diagram form the operation of the personal health digitizer of FIG. 8 that is used with the present information management system for personal health digitizers.

FIG. 8 illustrates an example of a specific personal health digitizer that is used with the present information management system for personal health digitizers; and FIG. 9 illustrates in flow diagram form the operation of the personal health digitizer of FIG. 8. In particular, the personal health digitizer 800 comprises a processor 811 that includes a microcontroller, Random Access Memory (RAM), as well as Read Only Memory (ROM) for storing the interpretive algorithms and driver software. The processor 811 is powered by a power source 810, and connected to a clock element 807 as well as a plurality of input/output devices. The input/output devices include a sensor element 801 that contains the electrodes used to perform the measurements of the desired physiological characteristics of the consumer. An Analog to Digital (A/D) Converter 804 functions to convert the analog measurement signals of sensor 801 to digital data that is used by processor 811 in its operation. The digital data is typically stored in non-volatile memory 809 and the processed data output displayed to the consumer on display 806 as well as transmitted to Information Management System IMS via Data Output Port 808 as described below. The personal health digitizer also optionally includes an audio output device 805 to provide the consumer with audible feedback.

The operation of the personal health digitizer 800 is illustrated in flow diagram form in FIG. 9 along with the partitioning of the data in memory 809. At step 901, the consumer activates the personal health digitizer 800 via appropriate operation of activation switches 802, 803 and places the sensor 801 in the required location to perform the desired measurements. At step 902, the personal health digitizer 800 acquires the measurement data and at step 903 converts this data into digital form by A/D converter 804 for use by processor 811. At step 904, processor 811 places a time and date stamp on the acquired data and stores this data in non-volatile memory 809 at step 905 in the "Uses Historic Data" partition on the memory 809. At step 906, processor 811 uses the interpretive algorithms to compare the presently acquired data with the Standard Reference Data and to analogous data points in the Users Historic Data. At step 907, the processor 811 applies the interpretive algorithms such as Boolean algebra, fuzzy logic, statistical analyses, and the like, to the acquired data and at step 908 matches the acquired data with appropriate "condition" and/or "diagnosis" which can be displayed to the consumer on display 806 at step 910. The acquired data along with the interpretive results can be stored in memory 809 and transmitted at step 909 via Data Output Port 808 as noted above. At step 911, the consumer operates appropriate ones of activation switches 802, 803 to power off the personal health digitizer 800.

In this manner, the physiological measurement data is acquired by the personal health digitizer, stored in memory and partially processed to provide the consumer with initial information. The acquired data can be transmitted to the Information Management System IMS each time the personal health digitizer 800 is operated, or on a data download basis where a plurality of data entries are transmitted to the Information Management System IMS, as desired by the consumer.

Reproductive Information Example of Analysis

By routing all personal health digitizer telecommunication traffic through the proprietary web site WS, cycle data may be stored in the underlying database 400. Interactive, directed health questionnaires will serve to relate the patterns to specific users without the need for personal demographic data, thus ensuring confidentiality. Each personal health digitizer T1 has an electronic serial number, ensuring non-duplication and user-specific data in these single-user devices. The "Ovulonics" database DB comprises thousands to hundreds of thousands or more of cycle patterns coupled to user-specific health data which then serves as the base for expert systems software directed at pattern recognition and interpretation—for fertility and infertility diagnosis, epidemiological trends based on age, health condition, etc.

Once acquired, the physiologic data in the proprietary "Ovulonics" database may serve a multitude of inquisitors. Assigning a user-access code to each class of inquisitor easily controls level of access and interpretation. The consumer communicating via the home-use personal health digitizer is automatically assigned an access code reflecting lay-user status. The lay-user code, coupled with the personal health digitizer's serial number allows web site query and response based on her individual pattern, providing, for example, interpretation against the broad base of patterns. The interpretation filters 404–406 are specific to each class of user access code. For lay-users, the restrictions inherent in their access codes will result in pattern interpretation that is expressed in general terms, in lay language with appropriate disclaimers and suggestions regarding supplemental medical practitioner interpretation. The users who are entitled to access to the system are:

Consumers who have purchased and registered a personal health digitizer

Physician care-providers who are registered as subscribers

Institutions who are registered as subscribers

Each user is assigned an access code. The consumer access code consists of the built-in code (serial number) inherent in the associated personal health digitizer T1. Registration of the personal health digitizer allows the consumer to include not only user-specific demographic information, but also an additional personal password to protect the consumer's data from unauthorized access. Providers and Institutions are provided with access codes that designate their user class.

The system components include a personal health digitizer that comprises an electronics-based biosensor that can measure a physiologic parameter, convert the measurement into digital information, store the digital information, then download or transmit the stored digital information for use in other applications. The system also includes terminal hardware that comprises either a personal computer, or a stand-alone dedicated terminal device, or a component within the personal health digitizer that processes the digital information and/or format this digital information for transmission to another node in the network. A router is provided in the form of an Internet Web site that routes the digital information and other communications traffic among the various system components and customers: consumer, provider, database, institution. The system database includes various data segments including, but not limited to:

Raw data

Demographic, user-specific data

User access codes

Registration/identification data for the personal health digitizers that are served by the system Diagnostic patterns User-specific disclaimers User-specific output formats Database Management System The database management system that is operational on the database 400 comprises analytical software that includes both the commercially available database software and custom software for the specific data analysis task. The software routines include but are not limited to:

Access Code Recognition Software 401—verifies that the inquiring user has an operative access code, confirms the code classification and routes the user's request to an Initial Output Filter Download Acceptance Software 402—accepts data for storage in the database, places the received data in a buffer file until the received data can be screened and processed for inclusion in the database Initial Output Filter 403—segregates the possible array of outputs as a function of access code and query. As an example, the initial output filter sets up the diagnostic query routine for a consumer who requests assistance with a diagnosis, while it responds to a provider who requests a therapeutic suggestion with both a diagnostic query routine and a therapeutic suggestion output.

Pattern Recognition Software 407—an artificial intelligence routine that takes the elements of a pattern and compares the graphic pattern against known diagnostic patterns to produce a diagnosis within certain confidence limits.

Consumer Query Output Filter 404 —this routine delimits the nature of the output report to the consumer, together with the appropriate suggested course of action and suitable disclaimers.

Provider Query Output Filter 405 —this routine delimits the nature of the output report to the provider, together with the appropriate suggested course of action and suitable disclaimers.

Institution Query Output Filter 406 —this routine delimits the nature of the output report to the institution, together with the appropriate suggested course of action and suitable disclaimers.

Consumer Query

Figure 2:
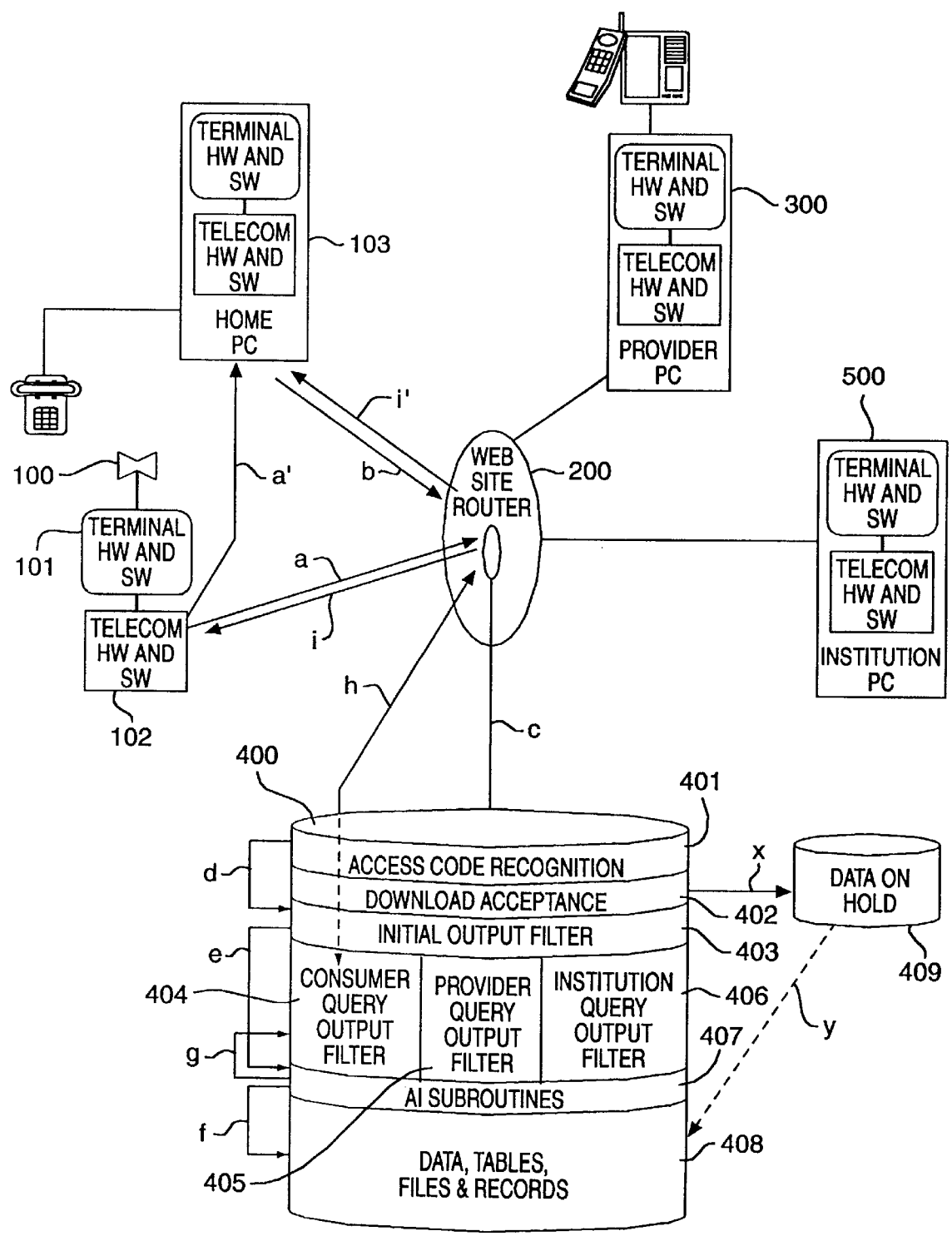
Figure 3:
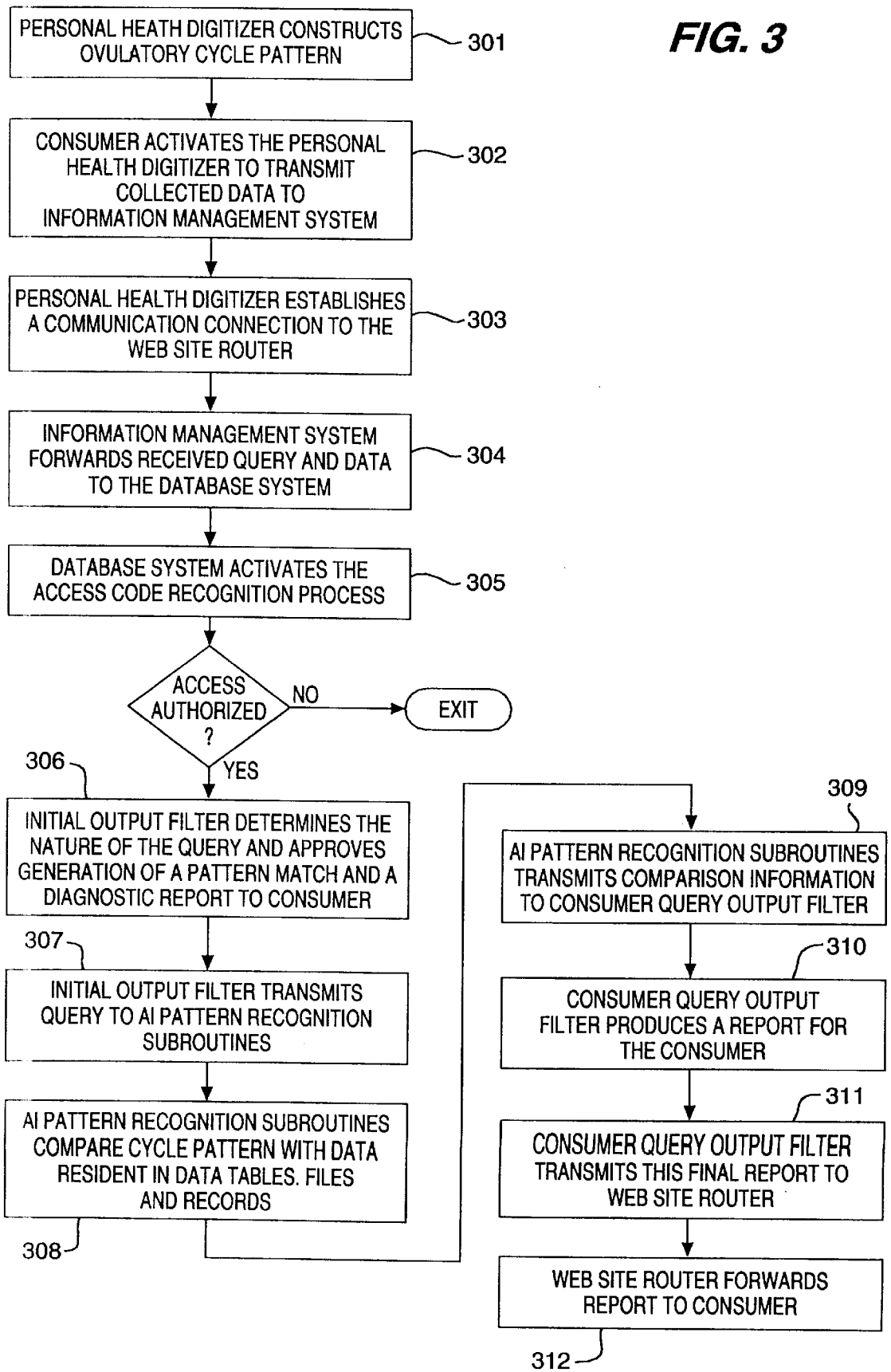

FIG. 2 illustrates the communication pathways that are used in the processing of a consumer query to the information management system IMS that is based upon personal health digitizer measurements, while FIG. 3 illustrates in flow diagram form the operation of this information management system IMS. For the purpose of illustration, the specific case is selected to be that of a consumer who has collected fertility data with a personal health digitizer 100 and is confused about the interpretation of the ovulatory cycle data that was performed by the personal heath digitizer 100. The consumer wishes to transmit the collected data from the personal heath digitizer 100 to the information management system IMS for verification of the interpretation and to obtain a more detailed interpretation.

At step 301 the personal heath digitizer 100, that is equipped with built in terminal hardware and software 101 and telecommunications hardware and software 102, constructs the present ovulatory cycle pattern from the readings that were performed by the personal heath digitizer 100 on the consumer and displays an interpretation of the computed ovulatory cycle pattern to the consumer. In the case where the consumer desires a more in-depth interpretation, the consumer at step 302 activates the personal heath digitizer 100 to transmit the collected data and a predetermined query that is programmed into the personal health digitizer 100 (or a query Formatted according to a user instruction manual) to the information management system IMS. This is accomplished by the personal heath digitizer 100 at step 303 activating the telecommunications software 102 resident in the personal heath digitizer 100 to establish a communication connection to the Web Site Router 200 over a standard communication connection, path (a). Once so connected, the personal heath digitizer 100 identifies itself by transmitting the personal health digitizer (PHD) serial number and registration data then downloads the collected data and the request for interpretation query to the information management system IMS. Alterative, the communications can be effected via the consumer's personal computer 103, wherein the collected data is transmitted via path (a') from the personal heath digitizer 100 to the personal computer 103 and thence via a communication connection over path (b) to the Web Site Router 200. In either case, at step 304, the information management system IMS forwards the received query and data over path (c) to the database system 400.

At step 305, the database system 400 activates the access code recognition process 401 which compares the received PHD serial number and registration data with consumer data stored in the database 400 to verify the both the nature of the requesting party (consumer) and the authorization of this consumer to access the services and data provided by the database 400. If the received data does not match the list of authorized consumers, the communication connection is rejected and the consumer disconnected. When the consumer is validated, the access code recognition process 401 forwards the received request over path (d) to the initial output filter 403. The initial output filter at step 306 determines the nature of the query and approves the generation of a standard pattern match and a diagnostic report to the consumer. This is accomplished at step 307 by transmitting the query that is received from the consumer in the proper format to the Artificial Intelligence (Al) Pattern Recognition Subroutines 407 via path (e). At step 308, the Al Pattern Recognition Subroutines 407 compare the cycle pattern generated by the consumer's personal heath digitizer 100 with the data resident in the Data Tables, Files and Records portion 408 of the database, which data is accessed via path (f). The data processing matches the consumer provided data with existing information that is stored in the database 400 and the Al Pattern Recognition Subroutines 407 produces a result that typically comprises a diagnosis, identification of a level of probability, identification of further possible actions that the consumer can take, and the like. At step 309, the Al Pattern Recognition Subroutines 407 transmits this information via path (g) to the Consumer Query Output Filter 404 which at step 310 determines the proper formatting and additional data that is needed to produce a report for the consumer. The report format and content is tailored to correspond to the query that was received from the consumer. For example, the raw data that is retrieved from the database 400 can comprise the following information:

anovulatory cycle—probability 0.94
luteal phase defect—probability 0.32
vaginal infection—probability 0.13
malfunction the personal heath digitizer—probability 0.021

The Consumer Query Output Filter 404 converts this raw data into a final report that is configured to be understandable by the consumer and contains appropriate recommendations and disclaimers. Such a report would typically be as follows:

Your request for cycle pattern clarification obtained by OvuSense #123456 was received on MM/DD/YY at HH:MM. Cycle data assessed covered the period from MM/DD/YY to MM/DD/YY. Cycle day 1 for this cycle was indicated as MM/DD/YY.

Analysis of your cycle data suggest that the following conditions or circumstances may have occurred, together with the estimated chance of that occurrence:

| Condition or Circumstance | Relative Probability |
| --- | --- |
| You may not have ovulated during this cycle | Highly likely |
| You may be having a problem with generating the proper hormones to prepare your uterus for conception | Moderately likely |
| You may have a vaginal infection that effected measurements during this cycle | Unlikely |
| Your OvuSense monitor may be malfunctioning | Highly unlikely |

This report Is meant to guide you In the interpretation of cycle patterns obtained from your OvuSense monitor. This report should be discussed with your physician, who is best suited to prescribe any further tests or treatment."

At step 311, the Consumer Query Output Filter 404 transmits this final report via path (h) to the Web Site Router 200 which forwards the report at step 312 to the consumer's personal heath digitizer 100 via path (I) or the consumers personal computer via path (I') for viewing by the consumer.

Consumer Query to a Physician, Who Queries Database

Figure 4:
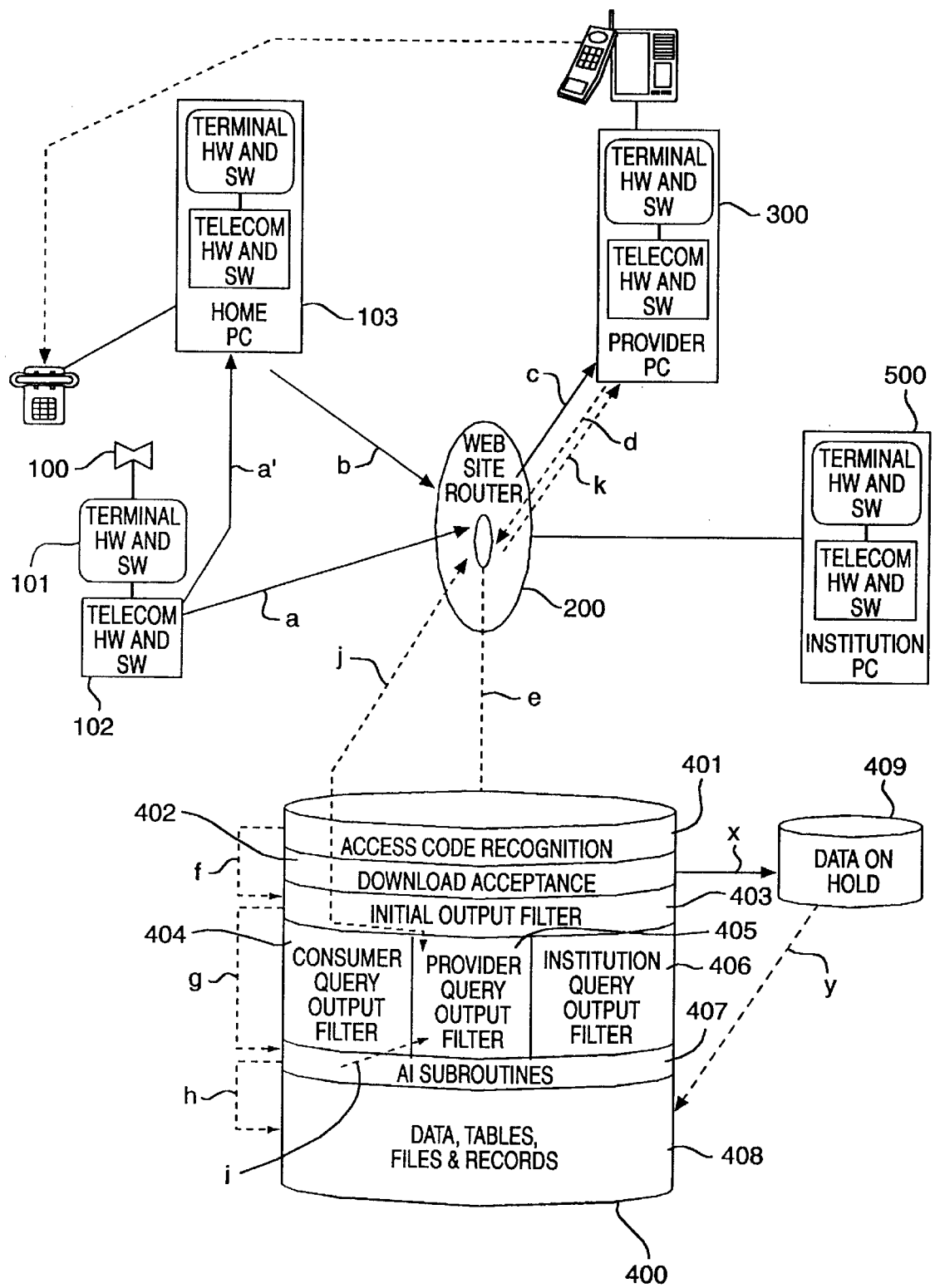
Figure 5B:
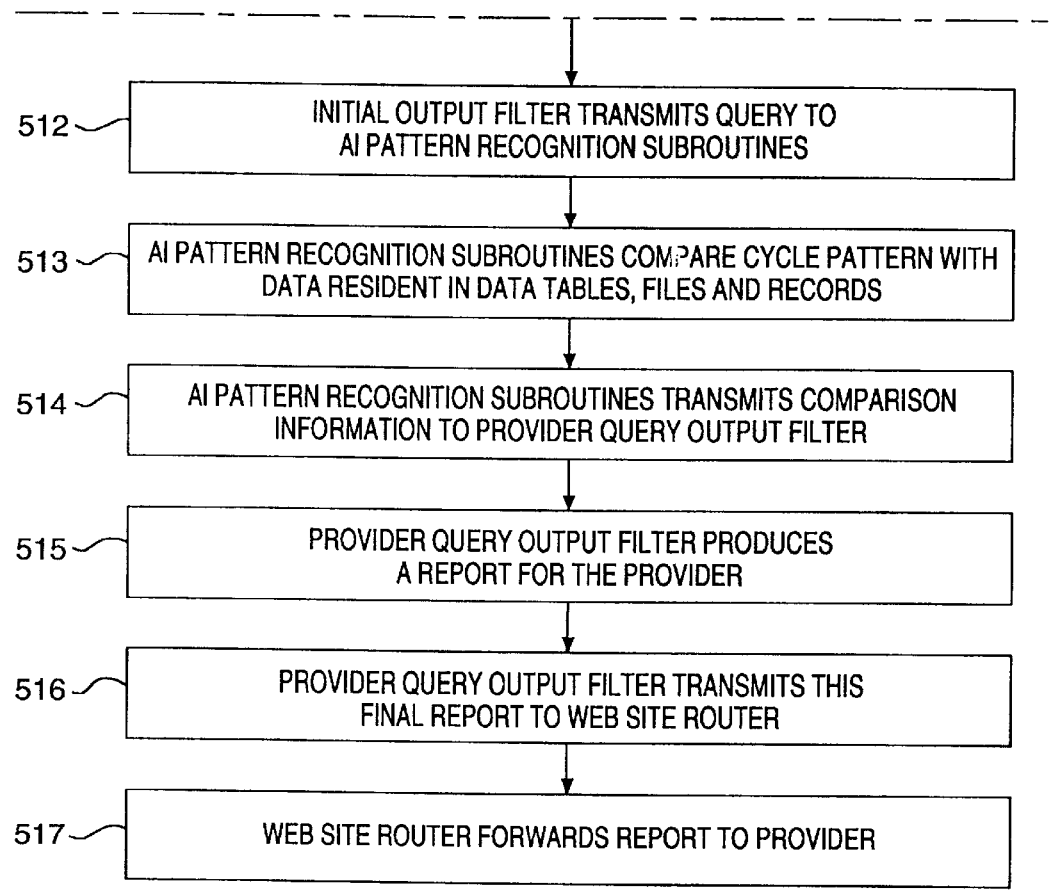

As an alternative to the consumer directly contacting the information management system IMS and obtaining a report, the consumer can contact a physician for a consult. FIG. 4 illustrates the communication pathways that are used in the processing of a combined consumer/physician query to the information management system IMS that is based upon personal health digitizer measurements, while FIGS. 5A and 5B illustrate in flow diagram form the operation of this information management system IMS.

For the purpose of illustration, the specific case noted above is selected to be that of a consumer who has collected fertility data with a personal health digitizer 100 and is confused about the interpretation of the ovulatory cycle data that was performed by the personal heath digitizer 100. The consumer wishes to transmit the collected data from the personal heath digitizer 100 to the consumer's physician for verification of the interpretation and to obtain a more detailed interpretation.

At step 501 the personal heath digitizer 100, that is equipped with built in terminal hardware and software 101 and telecommunications hardware and software 102, constructs the present ovulatory cycle pattern from the readings that were performed by the personal heath digitizer 100 on the consumer and displays an interpretation of the computed ovulatory cycle pattern to the consumer. The consumer desires a more in-depth interpretation and at step 502 activates the personal heath digitizer 100 to transmit the collected data to the physician via the information management system IMS. This is accomplished by the consumer selection the option that is preprogrammed into the personal health digitizer 100 that transmits the collected data to a predesignated physician via the information management system IMS. The selected physician is designated by the consumer, either on-line or at the time that the personal health digitizer 100 is first registered. This ensures that the consumer specific data is maintained in secrecy and not made available to other than consumer authorized physicians and/or health organizations. The personal heath digitizer 100 at step 503 activates the telecommunications software 102 resident in the personal heath digitizer 100 to establish a communication connection to the Web Site Router 200 over a standard communication connection indicate by path (a). Once so connected, the personal heath digitizer 100 identifies itself by transmitting the personal health digitizer (PHD) serial number and registration data, then downloads the collected data and a request for interpretation query to the information management system IMS. Alternatively, the communications can be effected via the consumer's personal computer 103, wherein the collected data is transmitted via pathway (a') from the personal heath digitizer 100 to the personal computer 103 and thence via a communication connection over path (b) to the Web Site Router 200. In either case, at step 504, the Web Site Router 200 receives the collected data as well as a request to transmit this collected data to an identified physician.

The Web Site Router 200 at step 505 activates the access code recognition process 401 which compares the received PHD serial number and registration data with consumer data stored in the database 400 to verify the both the nature of the requesting party (consumer) and the authorization of this consumer to access the data forwarding service provided by the information management system IMS. Furthermore, the access code recognition process 401 validates the identity of the identified physician to ensure that this physician is a subscriber to this service. ff the validation process fails, an error message is returned to the consumer and the communication connection dropped. Once the consumer is validated, the access code recognition process 401 at step 506 authorizes the Web Site Router 200 to store the received data in the database 400 and concurrently forward the received query and data over path (c) to the physician's personal computer 300 that is equipped with resident software that is used to perform an analysis of the collected data. The physician's personal computer 300 at step 507 displays the data and performs a limited analysis to thereby enable the physician to render a tentative diagnosis. If the physician desires to obtain a second opinion from the information management system IMS, the physician at step 508 transmits a provider query that is selected from a set of preprogrammed queries that are resident in the physician's terminal software, and the consumer's collected data via a communication connection over path (d) to the Web Site Router 200.

At step 509, the database system 400 activates the access code recognition process 401 via path (e) which compares the received provider access code data with provider data stored in the database 400 to verity the both the nature of the requesting party (provider) and the authorization of this provider to access the services and data provided by the database 400. If the received data does not match the list of authorized providers, the communication connection is rejected and the provider disconnected. Once the provider is validated, the access code recognition process 401 forwards at step 510 the received standard request over path (f) to the initial output filter 403. The initial output filter at step 511 determines the nature of the query and approves the generation of a pattern match and a diagnostic report to the provider. The processing of the request is accomplished at step 512 by transmitting the query that is received from the provider in the proper format to the Al Pattern Recognition Subroutines 407 via path (g). At step 513, the Al Pattern Recognition Subroutines 407 compare the cycle pattern generated by the consumer's personal heath digitizer with the data resident in the Data Tables, Files and Records portion 408 of the database, which data is accessed via path (h). The data processing matches the consumer provided data with existing information that is stored in the database and the Al Pattern Recognition Subroutines 407 produces a result that typically comprises a diagnosis, identification of a level of probability, identification of further possible actions that the provider can take, and the like. At step 514, the Al Pattern Recognition Subroutines 407 transmits this information via path (I) to the Provider Query Output Filter 405 which at step 515 determines the proper formatting and additional data that is needed to produce a report for the provider. For example, the raw data that is retrieved from the database can comprise the following information:

anovulatory cycle—probability 0.94
luteal phase defect—probability 0.32
vaginal infection—probability 0.13
malfunction the personal heath digitizer—probability 0.021

The Provider Query Output Filter 405 converts this raw data into a final report that is configured to be understandable by the provider and contains appropriate recommendations and disclaimers. Such a report can be as follows:

Your request for cycle pattern clarification obtained by OvuSense #123456 was received on MM/DD/YY at HH:MM. Cycle data assessed covered the period from MM/DD/YY to MM/DD/YY. Cycle day 1 for this cycle was indicated as MM/DD/YY.

Analysis of your cycle data suggest that the following conditions or circumstances may have occurred, together with the estimated chance of that occurrence:

| Condition or Circumstance | Relative Probability |
|---|---|
| Anovulatory cycle - | 0.94 |
| luteal phase defect | 0.32 |
| vaginal infection | 0.13 |
| malfunction the personal heath digitizer | 0.021 |

This report is meant to guide you in the interpretation of your patient's condition. This report should be assessed in the context of an appropriate medical history, a physical examination of the patient and suitable diagnostic tests.

At step 516, the Provider Query Output Filter 404 transmits this final report via path (j) to the Web Site Router 200 which forwards the report at step 517 to the physician's personal computer 300 via path (k) for viewing. The physician can then display the report, determine a care plan and telephone the consumer via path (I) to discuss the results.

Institution Query for Epidemiological Data

Figure 6:
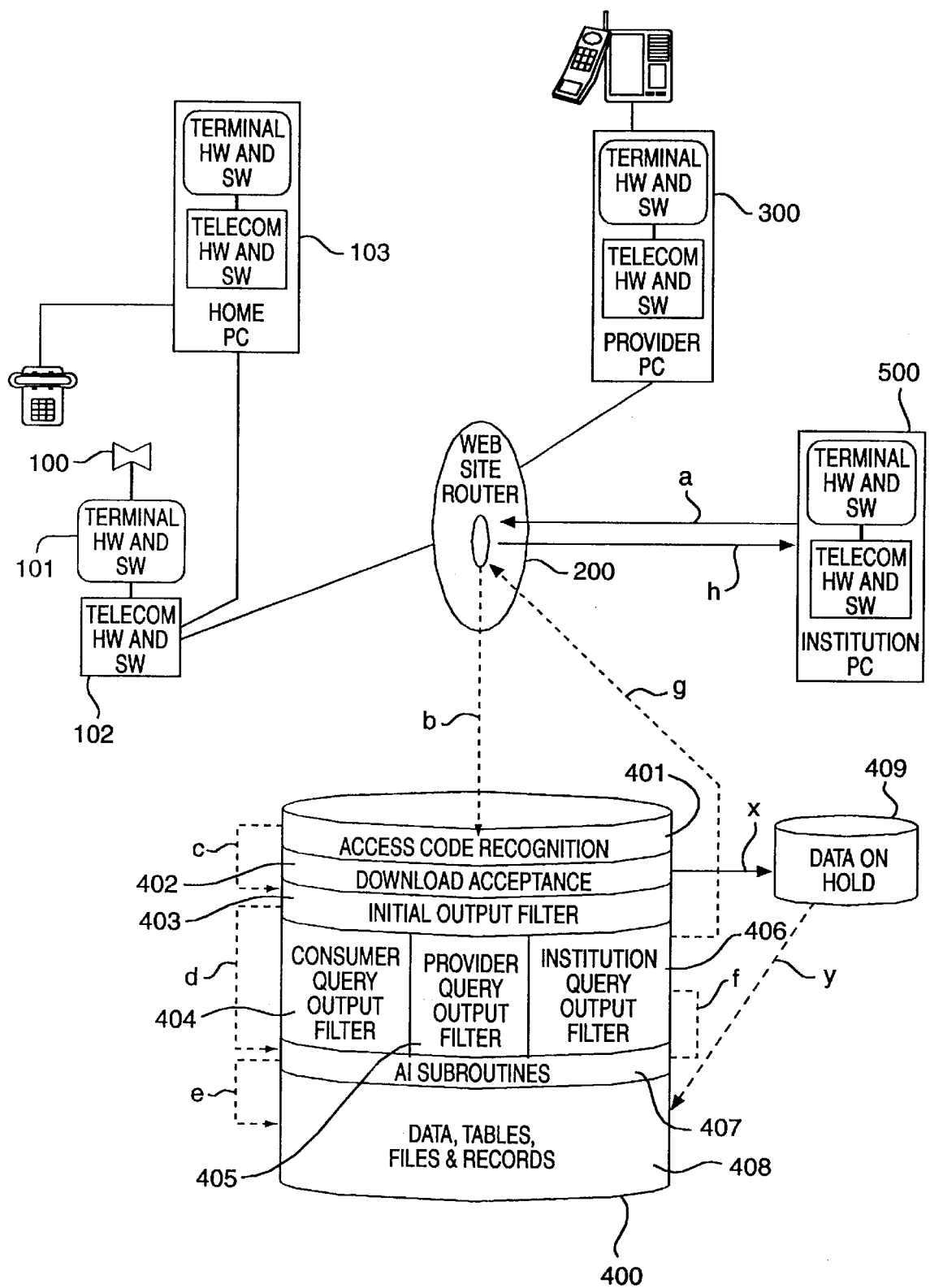
Figure 7:
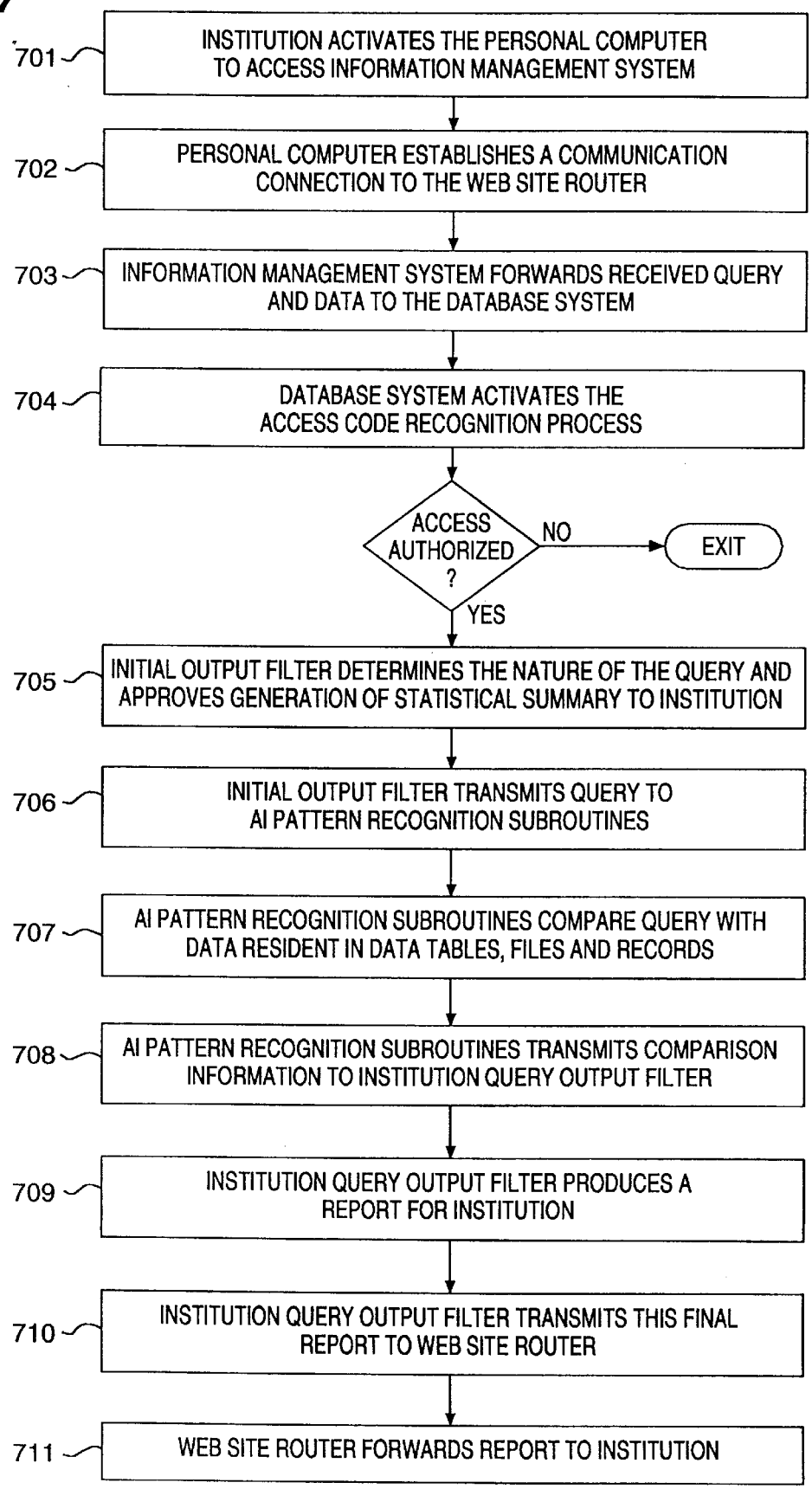

Another example of the use of the information management system IMS is where an institution, such as a managed care company, seeks information regarding fertility status among a population of reproductive age women in the New York state area, where the company is considering offering coverage for irnfertility care. In order to assess the economics of such coverage, the institution needs accurate actuarial data on the type of fertility problems exist and the frequency of such problems. FIG. 6 illustrates the communication pathways that are used in the processing of an institution query to the information management system IMS, while FIG. 7 illustrates in flow diagram form the operation of this information management system IMS.

At step 701 the institution activates the telecommunications software resident in the institution's personal computer 500 to establish a communication connection to the Web Site Router 200 over a standard communication connection via path (a). Once so connected, the personal computer 500 identifies itself by transmitting the institution's Institution Access Code and a request for information to the information management system IMS. At step 702, the Web Site Router 200 receives the request and forwards the received query over path (b) to the database 400. At step 703, the database system 400 activates the access code recognition process 401 which compares the received institution access code data with institution data stored in the database 400 to verify the both the nature of the requesting party (institution) and the authorization of this institution to access the services and data provided by the database 400. Once the institution is validated, the access code recognition process 401 forwards the received request over path (c) to the initial output filter 403. The initial output filter 403 at step 704 determines the nature of the query, which can be a query that was selected from a set of standard queries or one constrained to a predefined format to ensure privacy of the consumer-specific data, and approves the generation of a demographic report to the institution. The is accomplished at step 705 by transmitting the query that is received from the institution in the proper format to the AI Pattern Recognition Subroutines 407 via path (d). At step 706, the AI Pattern Recognition Subroutines 407 process the data resident in the Data Tables, Files and Records portion 408 of the database 400, which data is accessed via path (e). The data processing retrieves the demographic data and processes the raw data that is stored in the database 400 and the AI Pattern Recognition Subroutines 407 produces a result that typically comprises a set of composite statistics. At step 707, the AI Pattern Recognition Subroutines 407 transmits this information via path (f) to the Institution Query Output Filter 406 which at step 708 determines the proper formatting and additional data that is needed to produce a report for the institution. As part of this process, the Institution Query Output Filter 406 verifies that the data retrieved is not consumer-specific or of such limited scope as to compromise the privacy of the consumer-specific data. This process includes a determination of the size of the sample cohort, its respective size with respect to the overall target population, the topic areas that this institution is authorized to access, the specifics of the query, and the like.

For the purposes of illustrating this data processing, assume that the institution requested information on all OvuSense personal heath digitizer users resident in New York state who are between the ages of 20 and 35 and have normal ovulatory cycles, with greater than 10% anovulatory cycles, with possible polycystic ovary disease, and with luteal phase defects. The Institution Query Output Filter 406 is programmed to convert this information to institution-output format and apply certain recommendations and disclaimers. The final output is for example:

"Your request generated the following responses from the Ovulonics database as of MM/DD/YY:
Region: New York State
Female Population ages 20–35: 6,250,000
OvuSense users in database (sample size): 134,526
OvuSense users as a % of the specified cohort: 2.152%

Analysis of the requested data suggests that the following conditions or circumstances and their relative incidence, together with the estimated sampling error, exist within the specified cohort of OvuSense users:

| Condition or Circumstance | Number | Incidence (%) | Sampling Error (%) |
|---|---|---|---|
| Subjects having normal ovulation pattern | 115,080 | 85.54 | ±1.8 |
| Subjects with >10% anovulatory cycles | 11,232 | 8.35 | ±0.84 |
| Subjects with diagnosis consistent with polycystic disease | 5,761 | 4.28 | ±0.67 |
| Subjects with diagnosis consistent with luteal phase defect | 2,453 | 1.82 | ±0.35 |

This report is meant to serve as one method of epidemiological analysis. The data contained herein may contain bias and error not readily apparent. Conception Technology can take no responsibility for conclusions drawn from this data and report."

At step 709, the Institution Query Output Filter 406 transmits this final report via path (g) to the Web Site Router 200 which forwards the report at step 710 to the institution's personal computer 500 via path (h) for viewing.

Data Download Validation

In order to ensure the integrity of the data that is stored in the database 400, the information management system IMS includes a download acceptance process 402 that receives data that is transmitted by a consumer to the information management system IMS and stores the data via path (x) in a temporary file termed "data on hold 409" until the data can be validated. The validation process comprises a review of the format and content of the data to prevent bogus data from corrupting the integrity of the database 400. In particular, the consumer identification information as well as the associated measurement data is screened for data usability and associated demographic information. The proper formatting of the data is verified and then the received data is stored in the data on hold file 409. Once the data stored in this file is reviewed by either information management system IMS personnel and/or further validation software, it is downloaded via path (y) to the permanent data repository of data tables, files and records 408 where it is incorporated into the existing population of data.

Women's Health Care Examples

The above-description was focused on female reproductive measurements, but the concept of the information management system IMS is directly extensible to many areas of health. Some important subsectors that have been identified include, but are not limited to: reproductive health, cardiovascular disease, cancer detection and treatment, osteoporosis, urological conditions, and services. Examples of the major systems of interest are:

| | | |
|---|---|---|
| gastrointestinal | neurological | digestive |
| respiratory | musculoskeletal | endocrinic |
| reproductive | dermal/epidermal | immune |

Examples of the types of body fluids that are available for measurements are:

extra corporeal—saliva, mucous, urine, sweat, milk extracellular, intracellular, vaginal mucous, bronchial Furthermore, the vital signs —temperature, blood pressure, respirations, heart rate as well as electrochemical events —redox, ion transfer, ion channel, free radical measurements are subject to measurement by personal health digitizers.

SUMMARY

Thus, this system provides a centralized database that collects and stores monitoring data from a large number of individuals who are termed "consumers" herein. The information management system for personal health digitizers includes processing elements that perform statistical analysis of the collected data from any of numerous viewpoints, such as on a per consumer, population segment, or query specific basis. Thus, the information management system collects a statistically valid volume of data from numerous consumers and performs pattern matching and other statistical analyses on this data in a multi-dimensional manner to thereby deliver relevant information to the various classes of users who access the information management system.

What is claimed:

1. An interactive information management system for the collection and analysis of proprietary consumer specific data that is generated by a plurality of consumers located at remote sites using personal health digitizers, and for regulating user's access to the collected proprietary consumer specific data and results of the analysis by class of user, comprising:

means for establishing a data communication connection with a consumer's terminal equipment to input data from said consumer's personal health digitizer to said information management system;

means for storing data received from said consumer's personal health digitizer in a database;

means for processing said received data to identify patterns in said received data;

means for providing access to said received and processed data to an accessing user as a function of an identity of a one of a plurality of classes of users of which said accessing user is a member, comprising:

means for enabling a user to input a query relating to consumer specific data input to said information management system by said consumer, and means, responsive to said input query, for blocking intrusive access to said consumer specific data by said user inputting said query.

2. The system of claim 1 wherein said means for providing access further comprises:

means for enabling a consumer to authorize at least one user to access consumer specific data input to said information management system by said consumer.

3. The system of claim 1 wherein said means for blocking intrusive access comprises:

a plurality of input filters, each of which functions to provide limits to a quantity and content of said consumer specific data input by said consumer.

4. The system of claim 1 wherein said means for establishing a data communication connection comprises:

web site server means for providing users with a point of access to said information management system via Internet.

5. The system of claim 1 wherein said means for processing comprises:

at least one data interpretive system for identifying patterns in said received data.

6. A method of operating an interactive information management system for the collection and analysis of proprietary consumer specific data that is generated by a plurality of consumers located at remote sites using personal health digitizers, and for regulating user's access to the collected proprietary consumer specific data and results of the analysis by class of user, comprising the steps of:

establishing a data communication connection with a consumer's terminal equipment to input data from said consumers personal health digitizer to said information management system;

storing data received from said consumer's personal health digitizer in a database;

processing said received data to identify patterns in said received data;

providing access to said received and processed data to an accessing user as a function of an identity of a one of a plurality of classes of users of which said accessing user is a member comprising:

enabling a user to input a query relating to consumer specific data input to said information management system by said consumer, and blocking, in response to said input query, intrusive access to said consumer specific data by said user inputting said query.

7. The method of claim 6 wherein said step of providing access further comprises:

enabling a consumer to authorize at least one user to access consumer specific data input to said information management system by said consumer.

8. The method of claim 6 wherein said step of blocking intrusive access comprises:

activating a selected one of a plurality of input filters, each of which functions to provide limits to a quantity and content of said consumer specific data input by said consumer.

9. The method of claim 6 wherein said step of establishing a data communication connection comprises:

providing a web site server for users to provide a point of access to said information management system via Internet.

10. The method of claim 6 wherein said step of processing comprises:

activating at least one data interpretive system for identifying patterns in said received data.

11. An interactive information management system for the collection and analysis of proprietary consumer specific data that is generated by a plurality of consumers located at remote sites using personal health digitizers, and for regulating user's access to the collected proprietary consumer specific data and results of the analysis by class of user, comprising:

means for storing data received from said consumers' personal health digitizers in a database;

means for processing said received data to identify patterns in said received data; and means for providing access to said received and processed data to an accessing user as a function of an identity of a one of a plurality of classes of users of which said accessing user is a member comprising:

means for enabling a consumer to authorize at least one user to access consumer specific data input to said information management system by said consumer; and means for blocking intrusive access to said consumer specific data by said user.

12. The system of claim 11 wherein said means for blocking intrusive access comprises:

a plurality of input filters, each of which functions to provide limits to a quantity and content of said consumer specific data input by said consumer.

13. The system of claim 12 wherein said means for establishing a data communication connection comprises:

web site server means for providing users with a point of access to said information management system via Internet.

14. The system of claim 11 wherein said means for processing comprises:

at least one data interpretive system for identifying patterns in said received data.

15. A method of operating an interactive information management system for the collection and analysis of proprietary consumer specific data that is generated by a plurality of consumers located at remote sites using personal health digitizers, and for regulating user's access to the collected proprietary consumer specific data and results of the analysis by class of user, comprising:

storing data received from said consumers' personal health digitizers in a database;

processing said received data to identify patterns in said received data;

providing access to said received and processed data to an accessing user as a function of an identity of a one of a plurality of classes of users of which said accessing user is a member comprising:

enabling a consumer to authorize at least one user to access consumer specific data input to said information management system by said consumer, and blocking intrusive access to said consumer specific data by said user.

16. The method of claim 15 wherein said step of blocking intrusive access comprises:

activating a selected one of a plurality of input filters, each of which functions to provide limits to a quantity and content of said consumer specific data input by said consumer.

17. The method of claim 16 wherein said step of establishing a data communication connection comprises:

providing users with a web site server point of access to said information management system via Internet.

18. The method of claim 15 wherein said step of processing comprises:

operating at least one data interpretive system for identifying patterns in said received data.

* * * * *